United States Patent [19]

McGovern et al.

[11] Patent Number: 4,621,143

[45] Date of Patent: Nov. 4, 1986

[54] COCKROACH REPELLANTS

[75] Inventors: Terrence P. McGovern, Bowie, Md.; George S. Burden, Gainesville, Fla.

[73] Assignee: The United States of America as represented by the Secretary of Agriculture, Washington, D.C.

[21] Appl. No.: 625,329

[22] Filed: Jun. 27, 1984

[51] Int. Cl.$^4$ .............. C07C 103/133; C07C 103/158; C07D 295/18

[52] U.S. Cl. ..................... 546/245; 546/205; 546/226; 544/172; 544/188; 544/189; 544/190; 544/191; 544/192; 544/204

[58] Field of Search ............... 546/245, 205, 226

[56] References Cited

U.S. PATENT DOCUMENTS

| | | | |
|---|---|---|---|
| 2,798,061 | 7/1957 | Coover | 546/245 |
| 3,143,466 | 8/1964 | Abood | 546/245 |
| 3,219,659 | 11/1965 | Skau | 546/245 |
| 3,222,203 | 12/1965 | Skau | 546/245 |
| 3,407,205 | 10/1968 | Skau | 546/245 |
| 3,904,635 | 9/1975 | Senoo | 546/245 |
| 4,021,224 | 5/1977 | Pallos | 546/245 |
| 4,054,576 | 10/1977 | Baker | 546/226 |
| 4,107,320 | 8/1978 | Grivsky | 546/226 |
| 4,118,500 | 10/1978 | Mitzlaff | 546/226 |
| 4,209,446 | 6/1980 | Schulze | 546/245 |
| 4,291,041 | 9/1981 | McGovern | 546/205 |
| 4,389,401 | 6/1983 | Smolanoff | 546/245 |

OTHER PUBLICATIONS

Shriner, Fuson, Curtin, Systematic Identification of Organic Compounds; 4th ed., John Wiley & Sons Inc.; N.Y., 1956; p. 288.

McGovern, T. et al, J. Econ. Entomol., 67(5), 639–640 (1974).

Primary Examiner—C. Warren Ivy
Attorney, Agent, or Firm—Howard M. Silverstein; David G. McConnell; William E. Scott

[57] ABSTRACT

A number of novel amides were found to be highly effective as cockroach repellents.

12 Claims, No Drawings

COCKROACH REPELLANTS

BACKGROUND OF THE INVENTION

1. Field of the Invention

This invention relates to insect repellents and more particularly to certain novel compounds and compositions and their use as cockroach repellents.

2. Description of the Art

There is a definite need for cockroach repellents or formulations thereof that are effective and long lasting. Application of an efficient repellent to potential harborage areas of shipping cartons and assorted containers can prevent the distribution or movement of cockroaches from one area to another. A repellent can be used either alone or as one phase of an integrated control program in buildings, food- and drink-vending machines, assorted equipment, transportation systems, and other areas where cockroaches may be a problem. An effective cockroach repellent would act as an alternate non-insecticidal means of reducing insect depredation from that of conventional insecticides and would be particularly useful in areas where the application of toxicants would be severely limited. Its importance as a control agent will continue to increase as the cockroach develops insecticide resistance. Although the potential for such repellent chemicals in cockroach control has been recognized for sometime, few effective repellents have been reported and even fewer practical demonstrations of the use of such chemicals have been described (Soap and Sanitary Chemistry, 21, 129 and 157, 1945; Industrial Engineering Chemistry, 43, 1588, 1951; Journal of Economic Entomology, 45, 133, 1952; Pest Control, 28 (6), 14, 1960; Journal of Economic Entomology, 53, 805, 1960; Pest Control, 28, (8), 44, 46, 48, 50, 1960; Pest Control, 29, (6), 32, 1961; Pest Control, 30, (7), 14, 16, 18, 1962; Journal of Economic Entomology, 63, 429, 1970; Journal of Economic Entomology, 64, 576, 1971; Journal of Economic Entomology, 67, 639, 1974; Journal of Economic Entomology, 67, 71, 1974; Journal of Medical Entomology, 12, 259, 1975; Journal of Economic Entomology, 12, 387, 1975; Production Research Report Number 164, USDA, ARS, 1976).

SUMMARY OF THE INVENTION

An object of this invention is to provide a class of compounds that is useful as cockroach repellents and that can be readily synthesized from commercially available intermediates.

Another object is to provide cockroach repellents that are more effective than those reported previously.

Still another object is to provide a means of controlling cockroaches.

A further object is to provide a means of controlling cockroaches that is more effective and less hazardous to man and the environment than methods currently in use.

A still further object is to provide a cockroach repellent that can be used in conjunction with other control agents in an integrated program.

According to this invention, the above objects are accomplished by a number of novel compounds having the following formula, and suitable compositions which incorporate the compounds, and methods of using them as cockroach repellents:

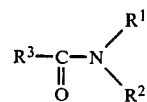

wherein $R^3$ is straight- or branched-chain alkyl having from 1 to 9 carbon atoms, straight- or branched-chain alkenyl having from 2 to 8 carbon atoms; halogen substituted straight- or branched-chain alkyl or alkenyl having from 1 to 3 carbon atoms; straight-chain alkyl having from 1 to 3 carbon atoms, one or more of which is substituted with an aromatic or alicyclic ring moiety which may be substituted with lower alkyl, lower alkenyl, halogen, or lower alkoxy to provide optimal repellency; or aromatic, alicyclic or bicyclic ring structures having from 3 to 7 carbon atoms and being optionally substituted with lower alkyl, lower alkenyl, halogen or lower alkoxy and wherein $R^1$ and $R^2$ taken together with the N represent an alkylene, an alkenylene, an alkyl substituted alkylene, an alkylene ether, an alkyl substituted alkylene ether, or an alkyl substituted alkylene ring structure and include the following:

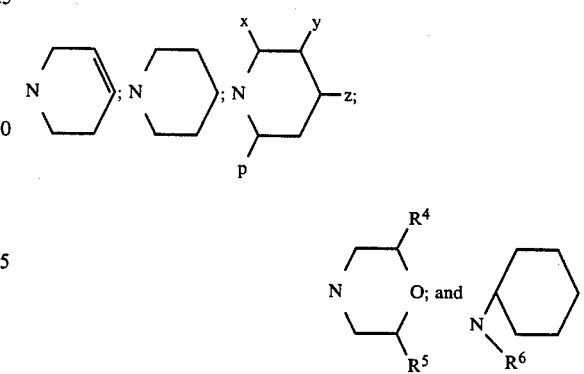

wherein when x is lower alkyl, y and z are hydrogen and p is either hydrogen or lower alkyl; and when x is hydrogen, each of y, z and p is individually lower alkyl or hydrogen and $R^4$, $R^5$ and $R^6$ are individually lower alkyl.

When $R^1$ and $R^2$ taken together with the N represent an alkylene or an alkyl substituted alkylene the structure can be depicted as

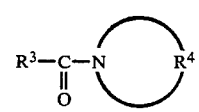

where $R^4$ is a $C_5$ alkylene or a lower alkyl substituted $C_5$ alkylene. For the purposes of this invention the terms lower alkyl, lower alkenyl, and lower alkoxy means the respective groups contain from 1 to 5 and preferably from 1 to 3 carbon atoms and are either straight- or branched-chained. Many of these compounds completely repel the German cockroach (Blattella germanica (L.) for prolonged periods under stringent test conditions. This species is among the most difficult of cockroach species to control.

The novel compounds of this invention are useful as cockroach repellents and certain of them are particularly effective against the German cockroach. The efficacy test that was used with these compounds is particularly stringent. In contrast to other test methods, where the cockroach is given an alternate choice of harborage, that is, a treated and an untreated refuge, the present method allows the insect no choice. The choice method will more frequently indicate a material is a good repellent than does the no-choice method because the stress that is exerted on the cockroach is much reduced, that is, the cockroach does not have to remain in the open. Then, under the no-choice test methods used with the compounds of this invention, if a chemical is 100% effective it means the chemical is a very strong repellent because it prevents all of the cockroaches in the test from entering a dark container that contains food and water and keeps them in an alien atmosphere. The cockroaches die rather than enter the chamber.

Bodenstein and Fales reported repellency data for 872 synthetic compounds against four species of cockroach using the less stringent tests noted above in which the roaches have a choice of harborages (Production Research Report No. 164, USDA, ARS, 1976). Sixty, 6.9%, of these provided one week of 100% protection against the German cockroach. These results testify to the unanticipated degree of effectiveness of the compounds of the present invention. Tables 1 and 2 show the effectiveness of 190 compounds as cockroach repellents; All 53 compounds in Table 1 provided seven days or more 100% repellency against the German cockroach, while the 137 compounds in Table 2 provided less than seven days, usually three days, or no repellency against the German cockroach. Therefore, out of 190 compounds, about 28% of them repelled 100% of the German cockroaches for a minimum of one week and 13 of the 53 compounds, about 24%, provided 100% protection for a minimum of either 14 or 17 days. In addition, the results shown in Tables 1 and 2 were obtained using the more stringent no-choice test described heretofore. A comparison of the compounds in Table 1 with those in Table 2 shows that many of them are homologs or otherwise very closely structurally related. However, the vast difference in the extent and degree of repellency of the compounds in each table is quite striking and is certainly strong evidence that the effectiveness of the 53 compounds in Table 1 could not have been anticipated.

Dead cockroaches are replaced at each reading period as noted later in the description of the test procedure. Overall mortality figures are included in Table 4 for repellents that lasted 17 days. These figures, when compared with the mortalities shown in Table 3 again emphasizes the effectiveness of these repellents. The cockroaches perish rather than enter the treated container. This effect becomes noticeable after about six days with an effective repellent.

Another example of the efficacy of the compounds in Table 1 is illustrated by the the data in Table 3 which was obtained using a commercial cockroach repellent, MGK-874 (2-hydroxyethyl-n-octyl sulfide), and subjecting it to the same rigorous tests that were used with the compounds of this invention. Method 1 duplicates the standard test used to evaluate the compounds of the present invention. The commercial repellent does not provide one day of 100% protection. Under the most accomodating situation, Method 4, it only provides two days of 100% protection which equals the repellent protection provided by the standard repellent, fencholic acid.

Because of the stringent nature of these tests, it is anticipated that the compounds of this invention will be even more effective in a natural environmental situation where the cockroaches do have many alternate choices for harborage other than areas protected by these repellents.

The German cockroach, the test species used in obtaining the efficiency data, is considered one of the most difficult to repel or to control. Chemicals found effective against this species are generally more effective against the three other major species found in the United States, the American cockroach, *Periplaneta americana* (L.), the oriental cockroach, *Blatta orientalis* (L.), and the brownbanded cockroach, *Supella longipalpa* (F.). A test procedure that includes these four cockroach species is based on this fact, (Journal of Economic Entomology, 67, 639, 1974, Journal of Economic Entomology, 63, 429, 1970, Journal of Medical Entomology 12, 259, 1975). It is anticipated the preferred compounds of this invention will also be highly effective against other cockroach species.

The compounds of this invention are amides which gives them the advantage of possessing the chemical stability associated with this type of chemical. Another advantage it has is that the pure chemical usually possesses little odor. The ease of preparation is a distinct advantage, usually requiring a one-step synthesis. Another advantage is that most of the acid or acid chloride and amine intermediates are available from commercial sources.

The amides were synthesized by the standard reaction between an acid chloride and an amine. The products were isolated by extraction procedures and purified by fractional distillation under high vacuum. A typical procedure is illustrated by the following description of the syntheses of 1-hexanoyl-1,2,3,6-tetrahydropyridine, compound 18 in Table 1: hexanoyl chloride, 27.0 grams (0.2 mole), was added dropwise to an ice cold solution (0° to 10° C.) of 1,2,3,6-tetrahydropyridine, 33.2 grams (0.4 mole) in 250 ml of anhydrous ether. The solution was stirred during the addition and then allowed to warm to ambient room temperature and to stand overnight. The crude product was washed sequentially with water, 5% hydrochloric acid, 5% sodium bicarbonate and with a saturated salt solution until the wash was neutral to litmus paper. After drying over anhydrous magnesium sulfate and filtering, the solvent was removed under reduced pressure (water aspirator). The crude amide was distilled under high vacuum to give 28.8 grams of product (b.p. 100° C./0.5 mm Hg; $n_{25}^D$ 1.4861).

The efficacy of the amides of the present invention was demonstrated by practical tests against the German cockroach. The effectiveness of the repellents was determined by ascertaining the minimum number of days the compounds repel 100% of the test cockroaches from a treated harborage containing food and water.

For the purpose of this invention, the compounds were applied as solutes in acetone. However, other compatible liquid or solid carriers may also be used.

TEST PROCEDURE

The chemicals were evaluated for repellent activity by the method of Burden and Eastin (Pest Control 28 (6), 14, 1960) with a slight revision. The inside walls of a 237-ml (0.5-pt) cylindrical paperboard carton were coated with 0.1 g of the candidate repellent dissolved in 5 ml of acetone. Food and water were placed inside the carton after the solvent had evaporated. The cockroaches were provided access to the darkened and baited interior of the carton via a 2.0-cm-diameter hole cut in the side of the carton. The carton was set in a glass utility jar (26.5 cm high×22.0 cm diameter) containing 25 adult male and female German cockroaches (12:13; reciprocal ratio in duplicate test). A 5-cm band of a mixture (1:1) of liquid and white petrolatum was applied along the top margin of the jar to prevent the cockroaches from escaping. Cockroaches in the treated carton were counted after 1,2,3, and 7 days, and every 3-4 days thereafter, until the compound became ineffective. Effectiveness was based on the length of time that 100% repellency was observed. The following classification system was used: Class 1, <100% repellency observed at intervals through seven days: Class 2, 100% repellency observed at all intervals through seven days; Class 3, 100% repellency observed at all intervals through 14 days; Class 4, 100% repellency observed at all intervals through 21 days; Class 5, 100% repellency observed at all intervals through 28 days. Dead cockroaches were replaced at three days and at each reading thereafter. All tests were duplicated and included a standard repellent, fencholic acid (3-isopropyl-1-methylcyclopentanecarboxylic acid), and an acetone check. The test environments were maintained at 27° C. and 60% RH in a daily light:dark regime of 8.5:15.5 hr, with two days of total darkness in each seven-day cycle of testing.

The foregoing examples of repellent action of these novel amides against cockroaches is meant to be illustrative rather than limiting. For example, the compounds of the present invention can be mixed with inert ingredients or with other known insect repellents. The compounds may also be formulated or embodied into repellent compositions in the form of creams, lotions, emulsions, suspensions, solutions, dusts, and aerosol or other type of sprays.

The compounds are usually applied in an effective cockroach repellent amount to the locus to be protected from infestation and, as noted above, can be applied in many varied forms to provide effective repellency. An effective cockroach repellent amount will vary greatly depending on the length of time that it is desired for it to be effective. The amount required in a particular situation can be readily ascertained by one skilled in the art. In a preferred method of application, the repellent compound is applied to the locus as a solution or suspension in a suitable solvent. The solutions or suspensions contain about 0.1 to 5.0%, preferably 0.5 to 2.0% by weight of the compound. A suitable solvent is any volatile solvent in which the compound is soluble and with which the compound will not react and which will not prevent the benefits of the invention from being realized.

TABLE 1

$$R^3-\underset{\underset{O}{\|}}{C}-N\begin{pmatrix}\\ \\\end{pmatrix}$$

| No. | $R^3$ | Repellency Class | Minimum No. of Days 100% Effective |
|---|---|---|---|
| 1 | 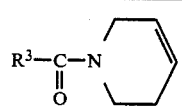 | 3 | 17 |
| 2 | $\underset{CH_3C=CH-}{\overset{H\ \ \ CH_3}{\phantom{x}\ \ \ |}}$ | 2 | 10 |
| 3 | $\underset{CHC=CH-}{\overset{CH_3}{|}}$ | 2 | 7 |
| 4 | $\underset{CH_2=C-}{\overset{CH_3}{|}}$ | 2 | 7 |
| 5 | $CH_3(CH_2)_2CH=CH-$ | 2 | 7 |
| 6 | $\underset{CH_3CH_2CH-}{\overset{CH_3}{|}}$ | 3 | 14 |
| 7 | $\underset{\underset{CH_3}{|}}{\overset{CH_3}{|}}CH_3C-$ | 2 | 10 |
| 8 | $\underset{CH_3(CH_2)_2CH-}{\overset{CH_3}{|}}$ | 3 | 14 |
| 9 | $\underset{CH_3CH(CH_2)_2-}{\overset{CH_3}{|}}$ | 2 | 10 |
| 10 | $\underset{\underset{CH_3}{|}}{\overset{CH_3}{|}}CH_3CHCH_2-$ | 3 | 14 |
| 11 | $\underset{CH_3CH_2CH-}{\overset{CH_2CH_3}{|}}$ | 3 | 17 |
| 12 | $\underset{\underset{CH_3}{|}}{\overset{CH_3}{|}}CH_3(CH_2)_2C-$ | 2 | 10 |
| 13 | $\underset{CH_3CH-}{\overset{CH_3}{|}}$ | 2 | 7 |
| 14 | $\underset{CH_3CHCH_2-}{\overset{CH_3}{|}}$ | 2 | 7 |
| 15 | $\underset{CH(CH_2)_3CH-}{\overset{CH_2CH_3}{|}}$ | 2 | 7 |
| 16 | $CH_3(CH_2)_2-$ | 2 | 10 |
| 17 | $CH_3(CH_2)_3-$ | 3 | 17 |
| 18 | $CH_3(CH_2)_4-$ | 2 | 7 |
| 19 | $CH_3(CH_2)_5-$ | 2 | 7 |
| 20 | $CH_3(CH_2)_6-$ | 3 | 14 |
| 21 | △- | 2 | 7 |
| 22 |  | 3 | 17 |

TABLE 1-continued

| No. | R³ | Repellency Class | Minimum No. of Days 100% Effective |
|---|---|---|---|
| 23 |  | 3 | 17 |
| 24 | 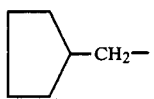 —CH₂— | 2 | 7 |
| | R³—C(=O)—N(piperidine) | | |
| 25 | 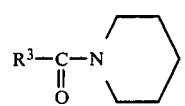 | 2 | 7 |
| 26 |  CH₃ | 2 | 10 |
| 27 | (CH₃)₂C=CH— | 2 | 7 |
| | R³—C(=O)—N(2-methylpiperidine) | | |
| 28 | 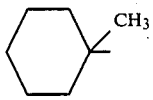 | 2 | 10 |
| 29 | 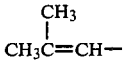 (cyclohexene) | 2 | 7 |
| 30 | 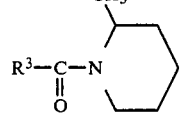 (norbornene) | 2 | 7 |
| 31 | (CH₃)₂C=CH— | 2 | 7 |
| 32 | CH₃CH=C(CH₃)— | 2 | 10 |
| | R³—C(=O)—N(3-methylpiperidine) | | |
| 33 |  | 2 | 10 |
| 34 |  (norbornene) | 2 | 10 |
| 35 | (CH₃)₂C=CH— | 2 | 10 |
| 36 | CH₃CH=C(CH₃)— | 2 | 7 |
| 37 | CH₃(CH₂)₂CH(CH₃)— | 2 | 7 |
| | R³—C(=O)—N(4-methylpiperidine) | | |
| 38 |  | 2 | 10 |
| 39 | 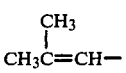 (cyclohexene) | 2 | 10 |
| 40 | 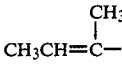 (norbornene) | 3 | 14 |
| 41 | (CH₃)₂C=CH— | 3 | 14 |
| 42 | CH₃CH=C(CH₃)— | 2 | 10 |
| 43 | CH₃(CH₂)₂CH(CH₃)— | 2 | 7 |
| | R³—C(=O)—N(2-ethylpiperidine) | | |
| 44 | (CH₃)₂C=CH— | 2 | 10 |
| 45 | CH₃CH=C(CH₃)— | 3 | 17 |

TABLE 1-continued

| No. | R³ | Repellency Class | Minimum No. of Days 100% Effective |
|---|---|---|---|

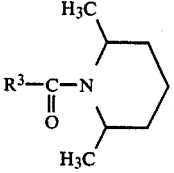

| 46 | 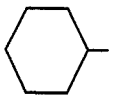 | 2 | 7 |
| 47 | CH₃CH=CH— with CH₃ branch (CH₃)₂C=CH— | 3 | 14 |
| 48 | CH₃CH=C(CH₃)— | 2 | 7 |
| 49 | CH₃CH₂— | 2 | 7 |

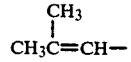

| 50 | 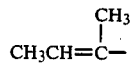 | 2 | 10 |

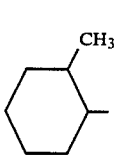

| 51 | CH₃— | 2 | 7 |
| 52 | CH₃CH₂— | 3 | 17 |
| 53 | CH₃(CH₂)₂— | 2 | 10 |

TABLE 2

| No. | R³ | Repellency Class |
|---|---|---|

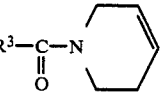

| 1 | 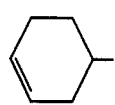 | 1 |
| 2 | 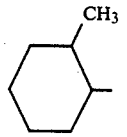 | 1 |

TABLE 2-continued

| No. | R³ | Repellency Class |
|---|---|---|
| 3 | 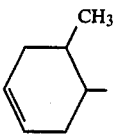 | 1 |
| 4 | 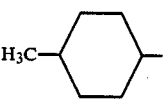 | 1 |
| 5 |  | 1 |
| 6 | 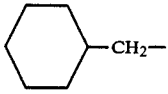 | 1 |
| 7 | 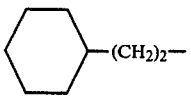 | 1 |
| 8 | (cyclohexyl)-(CH₂)₂— | 1 |
| 9 | (cyclohexyl)-(CH₂)₃— | 1 |
| 10 | 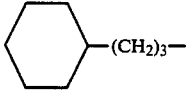 | 1 |
| 11 | CH₂=CH— | 1 |
| 12 | CH₃CH=CH— | 1 |
| 13 | CH₃CH₂CH=CH— | 1 |
| 14 | CH₃(CH₂)₃CH=CH— | 1 |
| 15 | CH₃(CH₂)₄CH=CH— | 1 |
| 16 | CH₃(CH₂)₅CH=CH— | 1 |
| 17 | CH₃— | 1 |
| 18 | CH₃CH₂— | 1 |
| 19 | CH₃(CH₂)₉— | 1 |
| 20 | CH₃(CH₂)₁₀— | 1 |
| 21 | CH₃(CH₂)₁₁— | 1 |
| 22 | CH₃(CH₂)₁₂— | 1 |
| 23 | CH₃(CH₂)₁₄— | 1 |
| 24 | CH₃(CH₂)₁₆— | 1 |
| 25 | 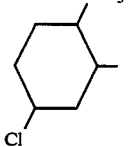 | 1 |

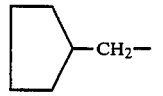

TABLE 2-continued

| No. | R³ | Repellency Class |
|---|---|---|
| 26 | 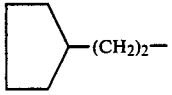 cyclopentyl-(CH₂)₂— | 1 |
| | $R^3-\underset{\underset{O}{\|\|}}{C}-N$ piperidine | |
| 27 | 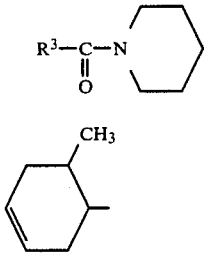 1,2-dimethylcyclohex-4-ene | 1 |
| 28 | 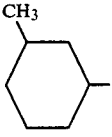 1,2-dimethylcyclohexane | 1 |
| 29 | 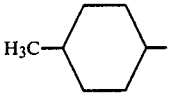 1,4-dimethylcyclohexane | 1 |
| 30 |  norbornene | 1 |
| 31 | 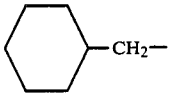 cyclohexyl-CH₂— | 1 |
| 32 | 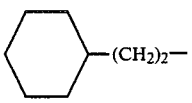 cyclohexyl-(CH₂)₂— | 1 |
| 33 | 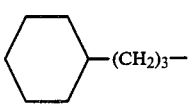 cyclohexyl-(CH₂)₃— | 1 |
| 34 | 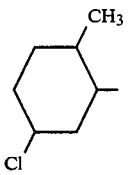 2-methyl-4-chlorocyclohexyl | 1 |
| 35 | CH₃CH=C(CH₃)— | 1 |
| 36 | CH₃CH₂CH(CH₃)— | 1 |
| 37 | CH₃(CH₂)₂CH(CH₃)— | 1 |

TABLE 2-continued

| No. | R³ | Repellency Class |
|---|---|---|
| 38 | 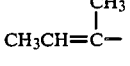 cyclopentyl-CH₂— | 1 |
| 39 | 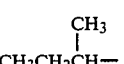 cyclopentenyl-CH₂— | 1 |
| 40 | 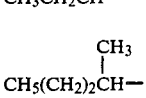 cyclopentyl-(CH₂)₂— | 1 |
| 41 | 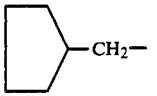 1,3,3-trimethylcyclopentyl | 1 |
| | $R^3-\underset{\underset{O}{\|\|}}{C}-N$ 2-methylpiperidine | |
| 42 | 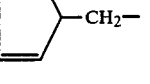 1,2-dimethylcyclohexyl | 1 |
| 43 | 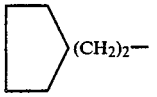 1,2-dimethylcyclohex-4-enyl | 1 |
| 44 | 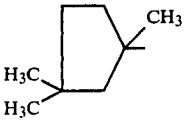 1,4-dimethylcyclohexyl | 1 |
| 45 | 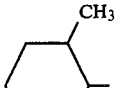 cyclohexyl-CH₂— | 1 |
| 46 | 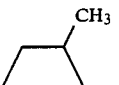 cyclohexyl-(CH₂)₂— | 1 |
| 47 | 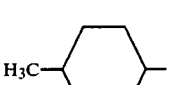 cyclohexyl-(CH₂)₃— | 1 |
| 48 | CH₃CH₂CH(CH₃)— | 1 |
| 49 | CH₃(CH₂)₂CH(CH₃)— | 1 |
| 50 | CH₃(CH₂)₉— | 1 |

TABLE 2-continued

| No. | R³ | Repellency Class |
|---|---|---|
| 51 | CH₃(CH₂)₁₀— | 1 |
| 52 | CH₃(CH₂)₁₁— | 1 |
| 53 | CH₃(CH₂)₁₂— | 1 |
| 54 | CH₃(CH₂)₁₄— | 1 |
| 55 | CH₃(CH₂)₁₆— | 1 |

$$R^3-\underset{O}{\underset{\|}{C}}-N\diagup\text{(3-methylpiperidine)}$$

| No. | R³ | Repellency Class |
|---|---|---|
| 56 | (cyclohexenyl) | 1 |
| 57 | (2-methylcyclohexyl) | 1 |
| 58 | (methylcyclohexenyl) | 1 |
| 59 | cyclohexyl-CH₂— | 1 |
| 60 | cyclohexyl-(CH₂)₂— | 1 |
| 61 | cyclohexyl-(CH₂)₃— | 1 |
| 62 | CH₃CH₂CH(CH₃)— | 1 |
| 63 | CH₃(CH₂)₉— | 1 |
| 64 | CH₃(CH₂)₁₀— | 1 |
| 65 | CH₃(CH₂)₁₁— | 1 |
| 66 | CH₃(CH₂)₁₂— | 1 |
| 67 | CH₃(CH₂)₁₄— | 1 |
| 68 | CH₃(CH₂)₁₆— | 1 |

$$R^3-\underset{O}{\underset{\|}{C}}-N\diagup\text{(4-methylpiperidine)}$$

| No. | R³ | Repellency Class |
|---|---|---|
| 69 | (2-methylcyclohexyl) | 1 |

TABLE 2-continued

| No. | R³ | Repellency Class |
|---|---|---|
| 70 | (methylcyclohexenyl) | 1 |
| 71 | cyclohexyl-CH₂— | 1 |
| 72 | cyclohexyl-(CH₂)₂— | 1 |
| 73 | cyclohexyl-(CH₂)₃— | 1 |
| 74 | CHCH₂CH(CH₃)— | 1 |
| 75 | CH₃(CH₂)₉— | 1 |
| 76 | CH₃(CH₂)₁₀— | 1 |
| 77 | CH₃(CH₂)₁₁— | 1 |
| 78 | CH₃(CH₂)₁₂— | 1 |
| 79 | CH₃(CH₂)₁₄— | 1 |
| 80 | CH₃(CH₂)₁₆— | 1 |

$$R_3-\underset{O}{\underset{\|}{C}}-N\diagup\text{(2-ethylpiperidine)}$$

| No. | R³ | Repellency Class |
|---|---|---|
| 81 | cyclohexyl | 1 |
| 82 | cyclohexenyl | 1 |
| 83 | (2-methylcyclohexyl) | 1 |
| 84 | (methylcyclohexenyl) | 1 |
| 85 | (norbornenyl) | 1 |

TABLE 2-continued

| No. | R³ | Repellency Class |
|---|---|---|
| 86 | cyclohexyl-CH₂— | 1 |
| 87 | cyclohexyl-(CH₂)₂— | 1 |
| 88 | cyclohexyl-(CH₂)₃— | 1 |
| 89 | CH₃CH₂CH(CH₃)— | 1 |
| 90 | CH₃(CH₂)₂CH(CH₃)— | 1 |
| 91 | CH₃(CH₂)₉— | 1 |
| 92 | CH₃(CH₂)₁₀— | 1 |
| 93 | CH₃(CH₂)₁₁— | 1 |
| 94 | CH₃(CH₂)₁₂— | 1 |
| 95 | CH₃(CH₂)₁₄— | 1 |
| 96 | CH₃(CH₂)₁₆— | 1 |
|  | R³—C(=O)—N(2,6-dimethylpiperidinyl) |  |
| 97 | cyclohexenyl— | 1 |
| 98 | 2-methylcyclohexyl— | 1 |
| 99 | methylcyclohexenyl— | 1 |
| 100 | norbornenyl— | 1 |
| 101 | cyclohexyl-CH₂— | 1 |
| 102 | cyclohexyl-(CH₂)₂— | 1 |
| 103 | cyclohexyl-(CH₂)₃— | 1 |
| 104 | CH₃CH₂CH(CH₃)— | 1 |
| 105 | CH₃(CH₂)₂CH(CH₃)— | 1 |
|  | R³—C(=O)—N(2,6-dimethylmorpholinyl) |  |
| 106 | cyclohexyl— | 1 |
| 107 | cyclohexenyl— | 1 |
| 108 | methylcyclohexenyl— | 1 |
| 109 | 4-methylcyclohexyl— | 1 |
| 110 | norbornenyl— | 1 |
| 111 | cyclohexyl-CH₂— | 1 |
| 112 | cyclohexyl-(CH₂)₂— | 1 |
| 113 | cyclohexyl-(CH₂)₃— | 1 |
| 114 | (CH₃)₂C=CH— | 1 |
| 115 | CH₃CH=C(CH₃)— | 1 |

TABLE 2-continued

| No. | R³ | Repellency Class |
|---|---|---|
| 116 | CH₃CH₂CH(CH₃)— | 1 |
| 117 | CH₃(CH₂)₂CH(CH₃)— | 1 |
| 118 | CH₃CH₂— | 1 |
| 119 | CH₃(CH₂)₉— | 1 |
| 120 | CH₃(CH₂)₁₀— | 1 |
| 121 | CH₃(CH₂)₁₁— | 1 |
| 122 | CH₃(CH₂)₁₂— | 1 |
| 123 | CH₃(CH₂)₁₄— | 1 |
| 124 | CH₃(CH₂)₁₆— | 1 |
| 125 | cyclopentyl-CH₂— | 1 |
| 126 | cyclopentenyl-CH₂— | 1 |
| 127 | cyclopentyl-(CH₂)₂— | 1 |

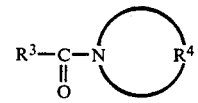

| 128 | CH₃(CH₂)₃— | 1 |
| 129 | CH₃(CH₂)₄— | 1 |
| 130 | CH₃(CH₂)₅— | 1 |
| 131 | CH₃(CH₂)₆— | 1 |
| 132 | CH₃(CH₂)₇— | 1 |
| 133 | CH₃(CH₂)₈— | 1 |
| 134 | CH₃(CH₂)₉— | 1 |
| 135 | CH₃(CH₂)₁₀— | 1 |
| 136 | CH₃(CH₂)₁₂— | 1 |
| 137 | CH₃(CH₂)₁₄— | 1 |

TABLE 3

| Method | % Inside Carton Day | | | | % Mortality | | | |
|---|---|---|---|---|---|---|---|---|
| | 1 | 2 | 3 | 7 | 1 | 2 | 3 | 7 |
| 1. Food & Water In Harborage | 1 | 8 | 10 | — | 0 | 0 | 0 | — |
| 2. Food in Harborage Water Out | 0 | 2 | .5 | 7 | 0 | 0 | 0 | 0 |
| 3. Water in Harborage Food Out | 1 | 4 | .5 | 13 | 0 | 0 | 0 | 1 |
| 4. Food & Water Out of Harborage | 0 | 0 | 2 | 6 | 0 | 0 | 0 | 0 |
| Fencholic acid Food, Water in Harborage | 0 | 0 | 10 | 80 | 0 | 0 | 0 | 0 |
| Check | 100 | 100 | 100 | 100 | 0 | 0 | 0 | 0 |
| (Acetone) | | | | | | | | |

TABLE 4

| Compound Number in Table 1 | % Mortality Total % of dead cockroaches replaced in the 17 to 21 day time period |
|---|---|
| 1 | 40.0 |
| 11 | 97.0 |
| 17 | 105.0 |
| 22 | 89.0 |
| 23 | 76.0 |
| 45 | 145.0 |
| 52 | 94.5 |

We claim:

1. A compound of the formula $$R^3-\underset{\underset{O}{\|}}{C}-N\bigcirc R^4$$

wherein R³ is one of the following groups:
  a. branched-chain alkyl having 3 to 5 carbon atoms;
  b. branched-chain alkenyl having 3 carbon atoms to thereby form a butenoic radical with the carbonyl group, wherein there is only one double bond and it is located at the 2 position;
  c. straight-chain alkyl having 1 to 3 carbon atoms, one or more of which is substituted with an alicyclic ring moiety which is substituted with lower alkenyl, halogen, or lower alkoxy;
  d. an alicyclic ring structure substituted with lower alkenyl, halogen or lower alkoxy;

wherein R⁴ is one of the following groups:
  a. C₅ alkylene;
  b. lower alkyl substituted C₅ alkylene.

2. The compound of claim 1 wherein R³ is an alicyclic ring structure or a branched-chain alkenyl, and

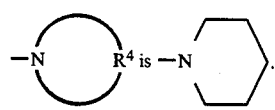

3. The compound of claim 1 wherein R³ is an alicyclic ring structure or a branched-chain alkenyl, and

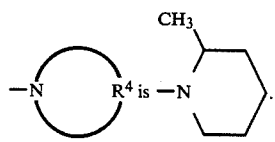

4. The compound of claim 1 wherein R³ is an alicyclic ring structure, or a branched-chain alkyl or alkenyl, and

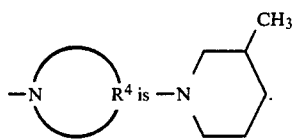

5. The compound of claim 1 wherein $R^3$ is an alicyclic ring structure, or a branched-chain alkyl or alkenyl, and

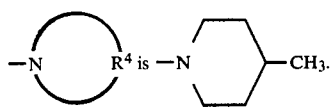

6. The compound of claim 5 wherein $R^3$ is

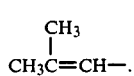

7. The compound of claim 1 wherein $R^3$ is a branched-chain alkenyl, and

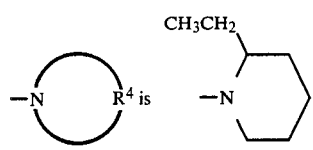

8. The compound of claim 7 wherein $R^3$ is

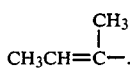

9. The compound of claim 1 wherein $R^3$ is an alicyclic ring structure or a branched-chain alkenyl, and

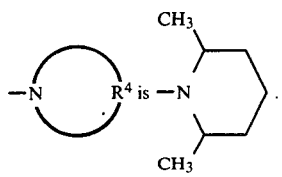

10. The compound of claim 9 wherein $R^3$ is

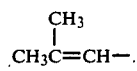

11. The compound of claim 1 wherein

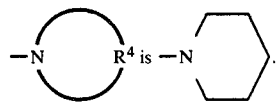

12. The compound of claim 1 wherein

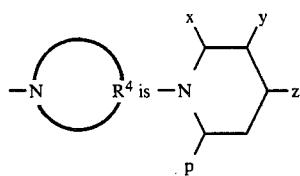

wherein x is lower alkyl, y and z are hydrogen and p is either hydrogen or lower alkyl, and when x is hydrogen, each of y, z and p is individually lower alkyl or hydrogen.

* * * * *